(12) United States Patent
McMillan et al.

(10) Patent No.: US 11,557,399 B2
(45) Date of Patent: Jan. 17, 2023

(54) INTEGRATIVE MACHINE LEARNING FRAMEWORK FOR COMBINING SENTIMENT-BASED AND SYMPTOM-BASED PREDICTIVE INFERENCES

(71) Applicant: Optum, Inc., Minnetonka, MN (US)

(72) Inventors: Corey D. McMillan, Salisbury, NC (US); William Alexander Wood, Fort Mill, SC (US); Austin Schick, Cary, NC (US); Donald Landrum, Gainesville, GA (US); Columbus Dong, Manteo, NC (US); Rachel Szabo, Pittsburgh, PA (US); William Drayton Taylor, Boston, MA (US); Austin T. Gansz, Schwenksville, PA (US)

(73) Assignee: Optum, Inc., Minnetonka, MN (US)

( * ) Notice: Subject to any disclaimer, the term of this patent is extended or adjusted under 35 U.S.C. 154(b) by 313 days.

(21) Appl. No.: 16/862,943

(22) Filed: Apr. 30, 2020

(65) Prior Publication Data
US 2021/0343406 A1 Nov. 4, 2021

(51) Int. Cl.
G06F 16/00 (2019.01)
G16H 50/20 (2018.01)
G06F 16/242 (2019.01)
G06N 20/00 (2019.01)
G06F 40/289 (2020.01)

(52) U.S. Cl.
CPC .......... *G16H 50/20* (2018.01); *G06F 16/244* (2019.01); *G06F 40/289* (2020.01); *G06N 20/00* (2019.01)

(58) Field of Classification Search
None
See application file for complete search history.

(56) References Cited

U.S. PATENT DOCUMENTS 9,536,049 B2   1/2017   Brown et al.
2005/0086082 A1   4/2005   Braunstein et al.

OTHER PUBLICATIONS

"Sentiment Analysis," (2 pages), (article, online). [Retrieved from the Internet Jul. 23, 2020] <URL: https://rstudio-pubs-static.s3.amazonaws.com/327619_9b746f2d0f6c4fc68ff325cc1dab3156.html>.
"SentiMentum," (3 pages), (article, online). [Retrieved from the Internet Jul. 23, 2020] <https://github.com/jamiekimyu/sentiNote>.

(Continued)

*Primary Examiner* — Bai D Vu
(74) *Attorney, Agent, or Firm* — Alston & Bird LLP

(57) ABSTRACT

Techniques for integrative machine learning using sentiment-based predictive inferences and symptom-based predictive are discussed herein. In one example, a method includes determining, based on one or more health monitoring logs, a first distribution of symptomatic prediction labels over a first period of time associated with the one or more health monitoring logs; processing the one or more health monitoring logs and using a sentiment detection machine learning model to determine a second distribution of extracted sentiment scores over the first period of time; generating, based on the first distribution and the second distribution, an aggregate distribution of inferred health-related predictions over the first period of time; and causing display of an aggregate distribution user interface that is configured to display the aggregate distribution.

20 Claims, 14 Drawing Sheets

(56) References Cited

OTHER PUBLICATIONS

Microsoft Health Bot Service, "Health Bot Overview," Dec. 12, 2017, (6 pages), (article, online). [Retrieved from the Internet Jul. 23, 2020] <URL: https://docs.microsoft.com/en-us/healthbot/>.
Penzu, "Health Diary," (3 pages), (article, online). [Retrieved from the Internet Jul. 23, 2020] <URL: https://penzu.com/health-diary>.
Wong, L.P. "Data Analysis In Qualitative Research: A Brief Guide To Using NVIVO," Malaysian Family Physician, (2008), vol. 3, No. 1, pp. 14-20, ISSN: 1985-207X.
Your.MD, "Symptom Checker," (8 pages), (article, online). [Retrieved from the Internet Jul. 23, 2020] <https://www.your.md/>.

INTEGRATIVE MACHINE LEARNING FRAMEWORK FOR COMBINING SENTIMENT-BASED AND SYMPTOM-BASED PREDICTIVE INFERENCES

BACKGROUND

Various embodiments described herein relate generally to systems and methods of machine learning, particularly in the context of machine learning tools used to parse and analyze unstructured, natural-language content on a longitudinal basis to extract predictively relevant data and transform such extracted information into a targeted, human-readable summary.

BRIEF SUMMARY

In general, embodiments of the present invention provide methods, apparatus, systems, computing devices, computing entities, and/or the like for generating one or more health-related predictive inferences from one or more health monitoring logs (e.g., one or more user-entered health monitoring logs, one or more provider-entered health monitoring logs, one or more patient-entered health monitoring logs, and/or the like).

In accordance with one aspect, a method is provided. In one embodiment, the method comprises determining, based on the one or more health monitoring logs, a first distribution of symptomatic prediction labels over a first period of time associated with the one or more health monitoring logs; determining, based on the one or more health monitoring logs, a second distribution of extracted sentiment scores over the first period of time; and generating, based on the first distribution and the second distribution, an aggregate distribution of inferred health-related predictions over the first period of time.

In accordance with another aspect, a computer program product is provided. The computer program product may comprise at least one computer-readable storage medium having computer-readable program code portions stored therein, the computer-readable program code portions comprising executable portions configured to determine, based on the one or more health monitoring logs, a first distribution of symptomatic prediction labels over a first period of time associated with the one or more health monitoring logs; determine, based on the one or more health monitoring logs, a second distribution of extracted sentiment scores over the first period of time; and generate, based on the first distribution and the second distribution, an aggregate distribution of inferred health-related predictions over the first period of time.

In accordance with yet another aspect, an apparatus comprising at least one processor and at least one memory including computer program code is provided. In one embodiment, the at least one memory and the computer program code may be configured to, with the processor, cause the apparatus to determine, based on the one or more health monitoring logs, a first distribution of symptomatic prediction labels over a first period of time associated with the one or more health monitoring logs; determine, based on the one or more health monitoring logs, a second distribution of extracted sentiment scores over the first period of time; and generate, based on the first distribution and the second distribution, an aggregate distribution of inferred health-related predictions over the first period of time.

BRIEF DESCRIPTION OF THE DRAWINGS

Figure 1:
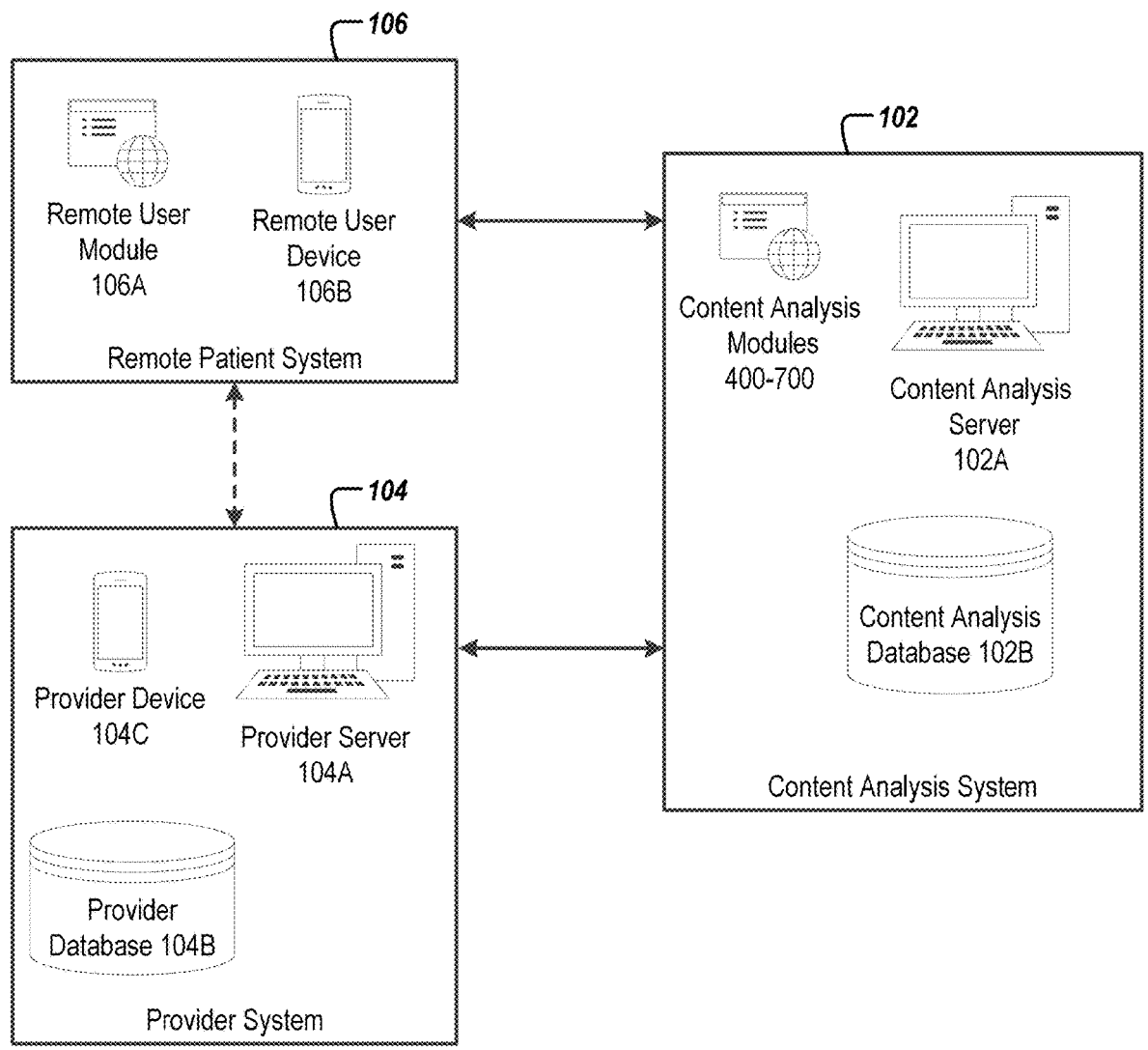
Figure 2:
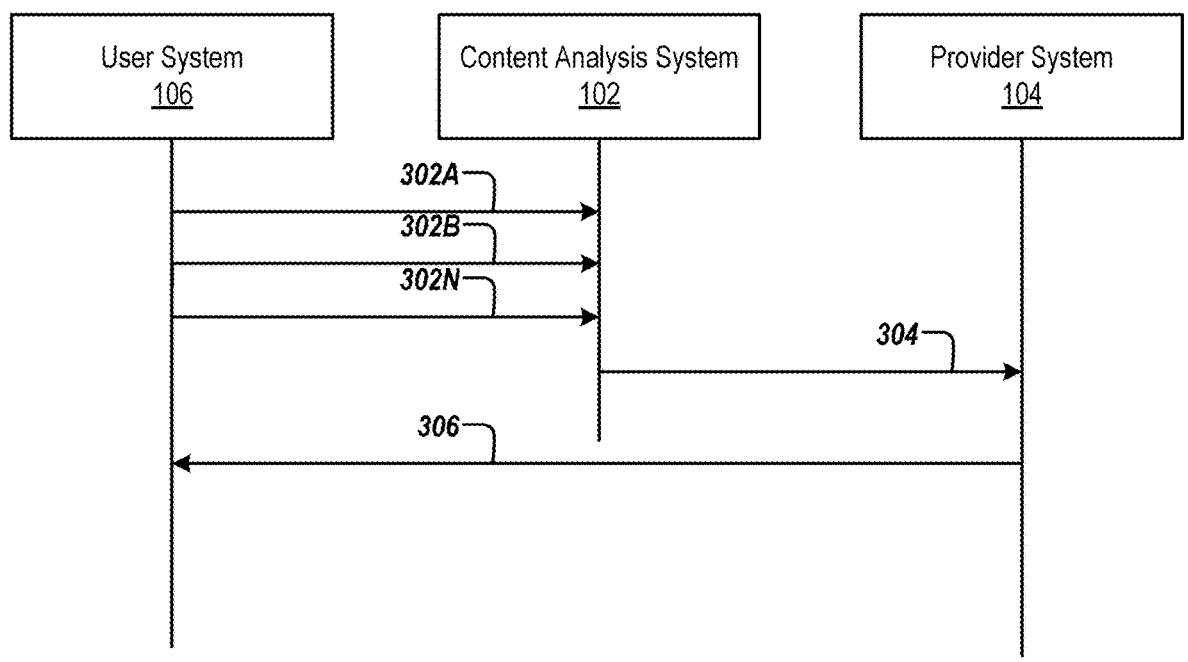
Figure 3:
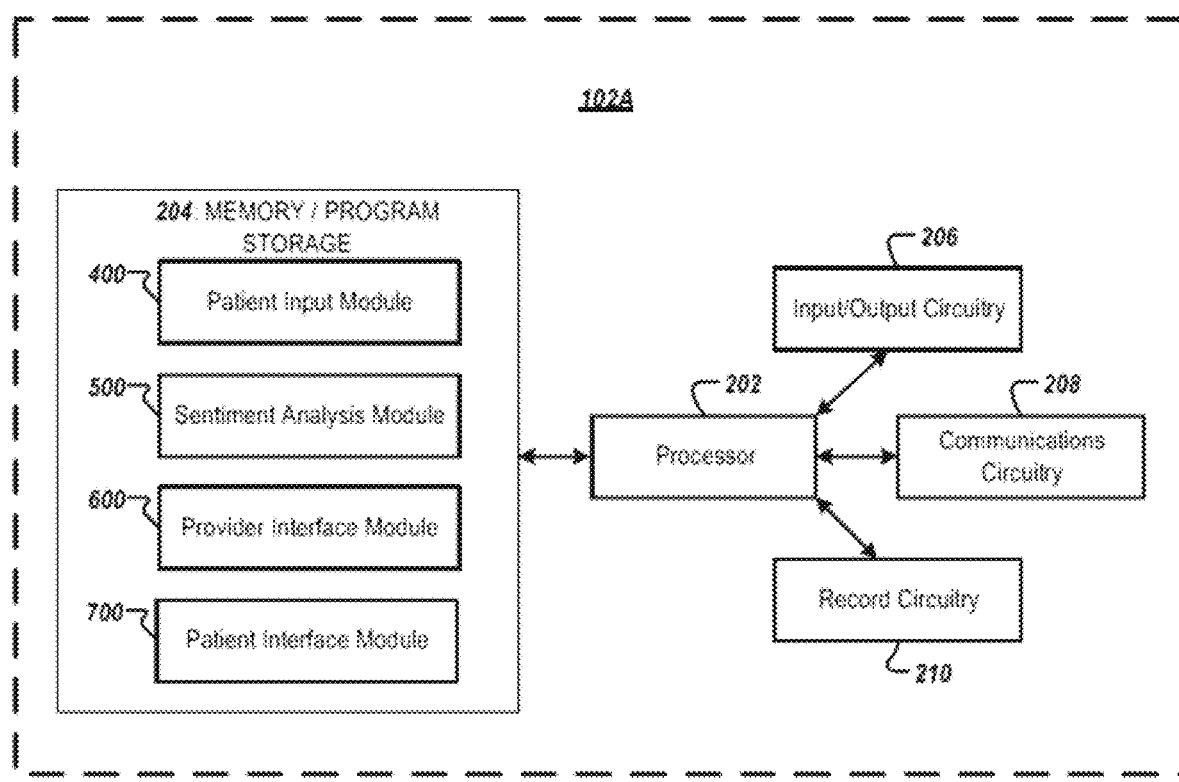
Figure 4:
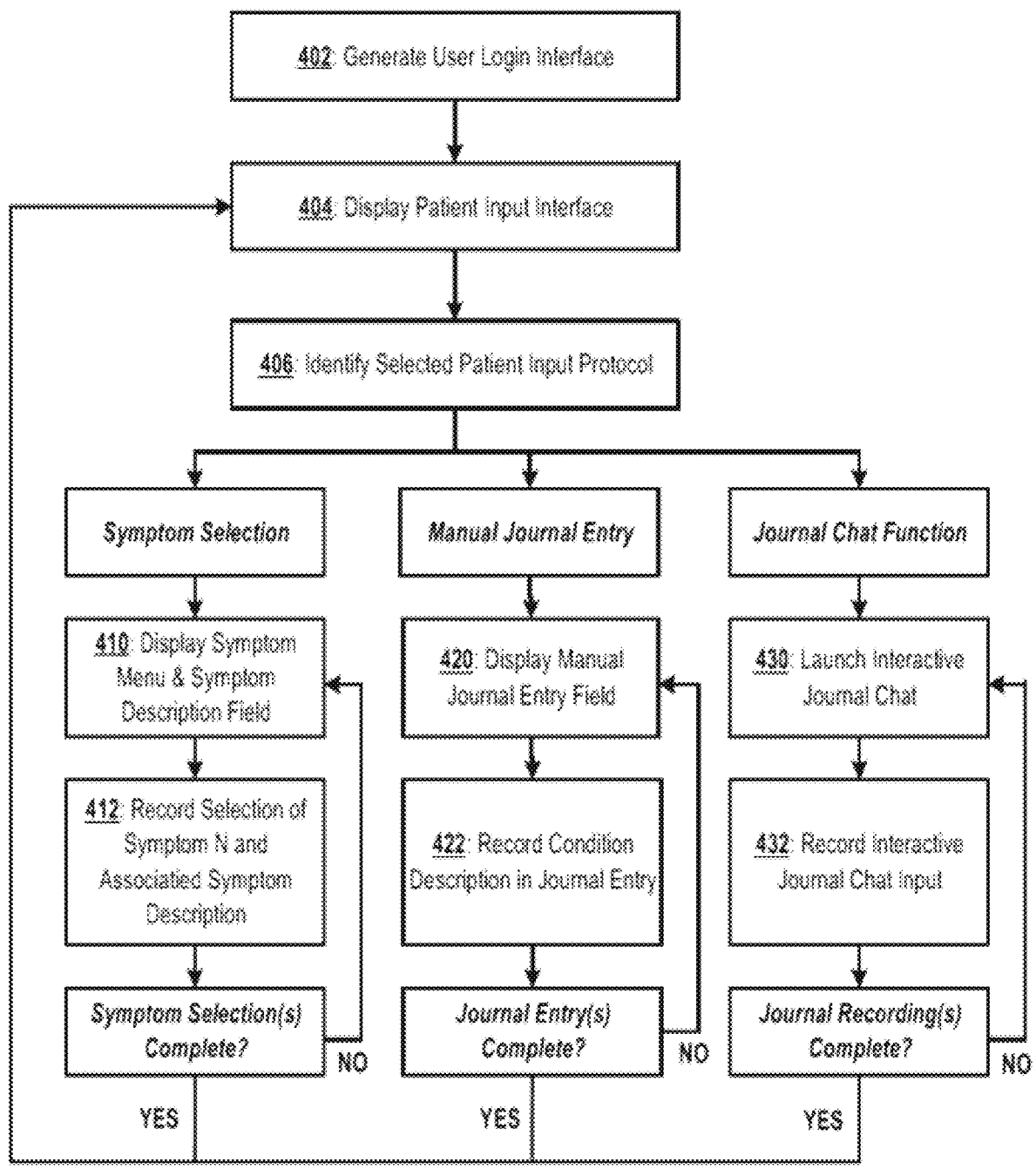
Figure 5:
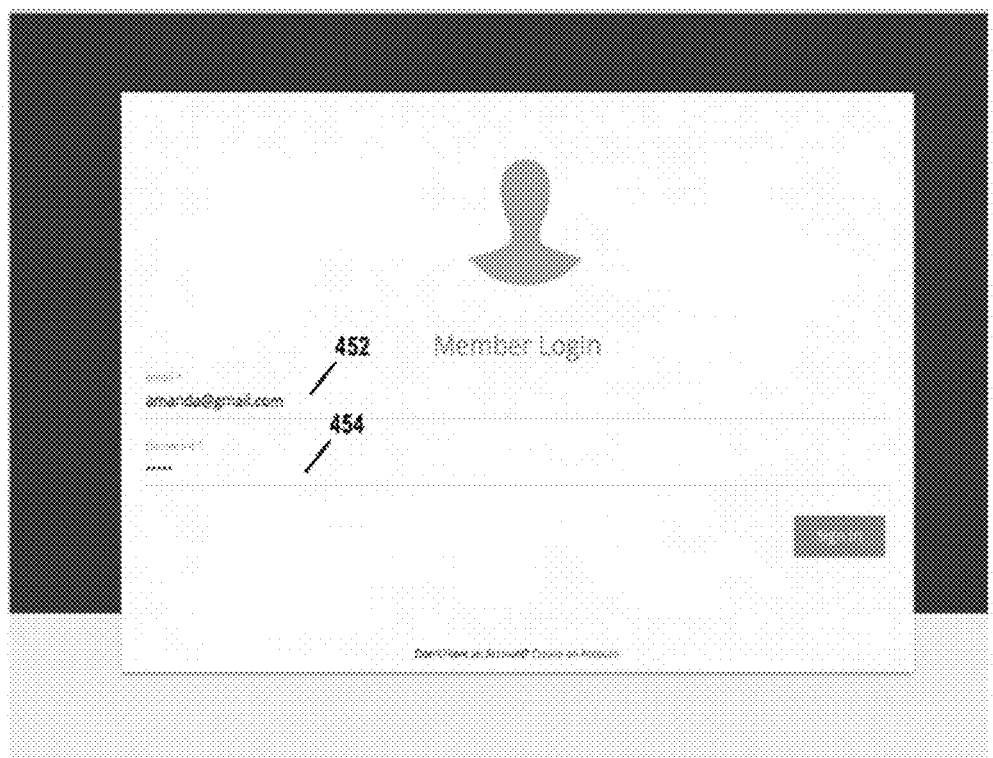
Figure 6A:
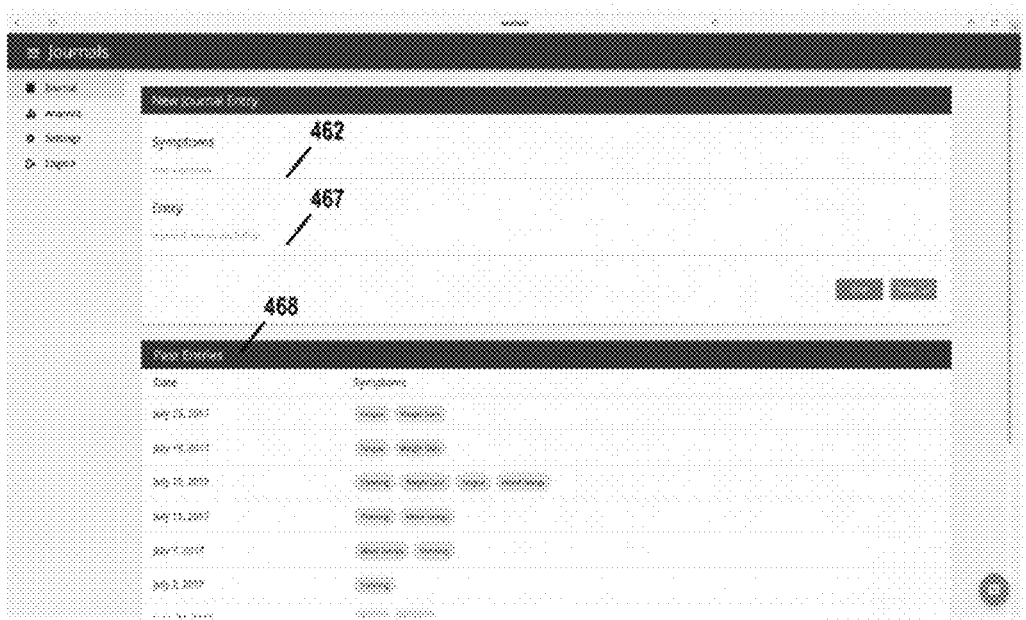
Figure 6B:
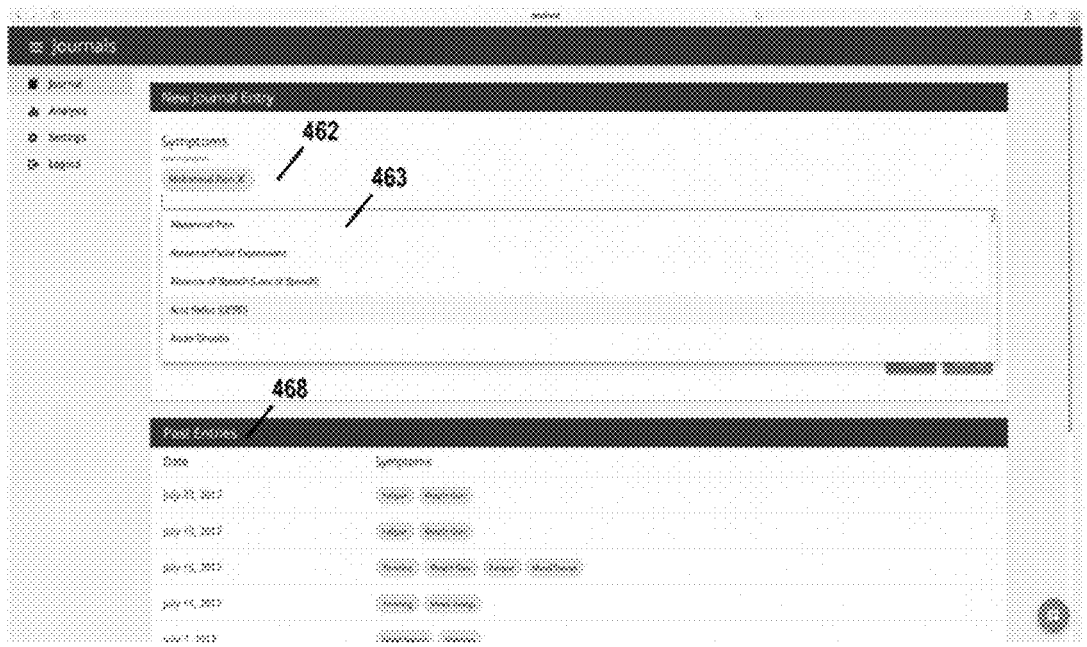
Figure 7:
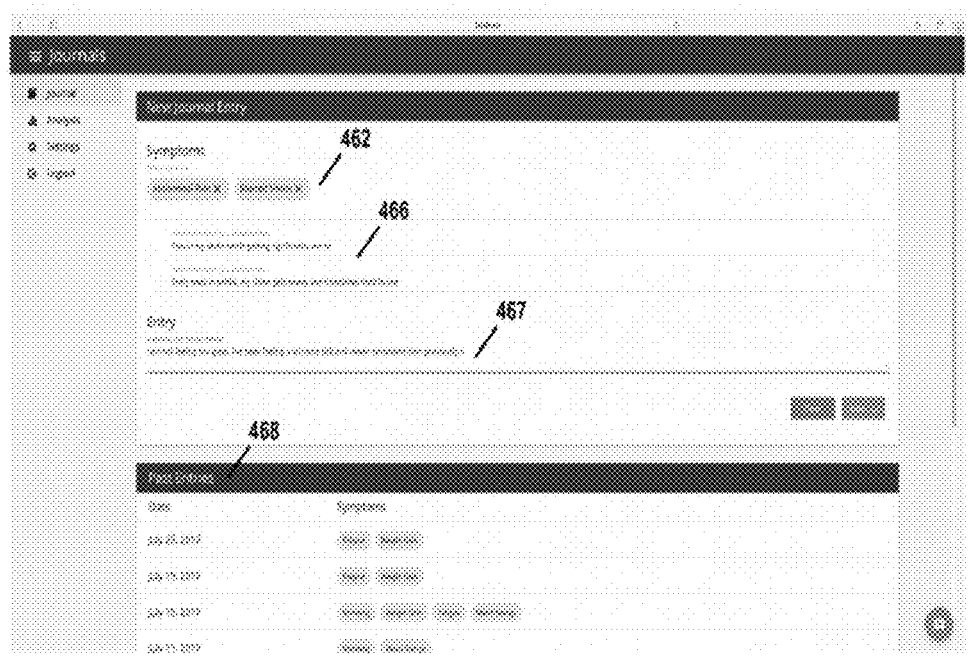
Figure 8:
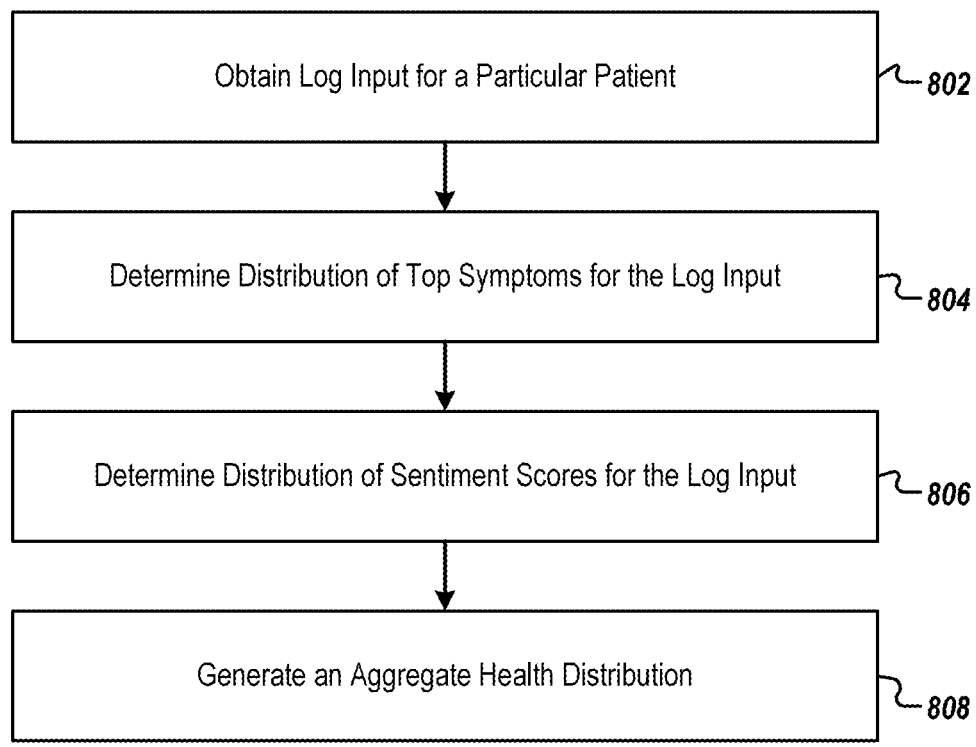
Figure 9:
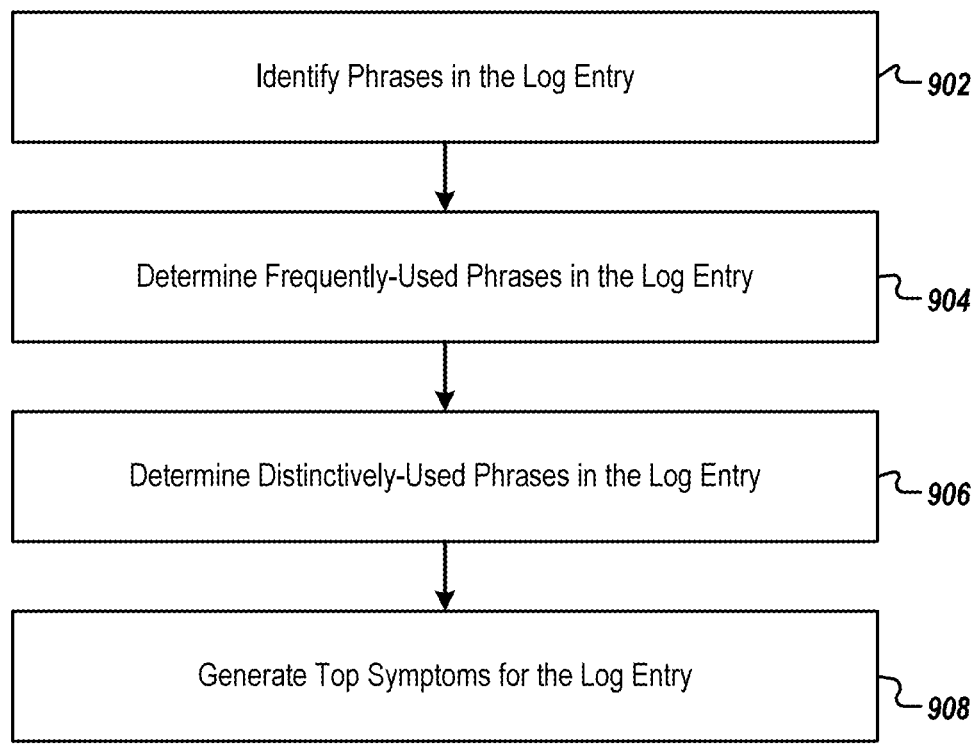
Figure 10:
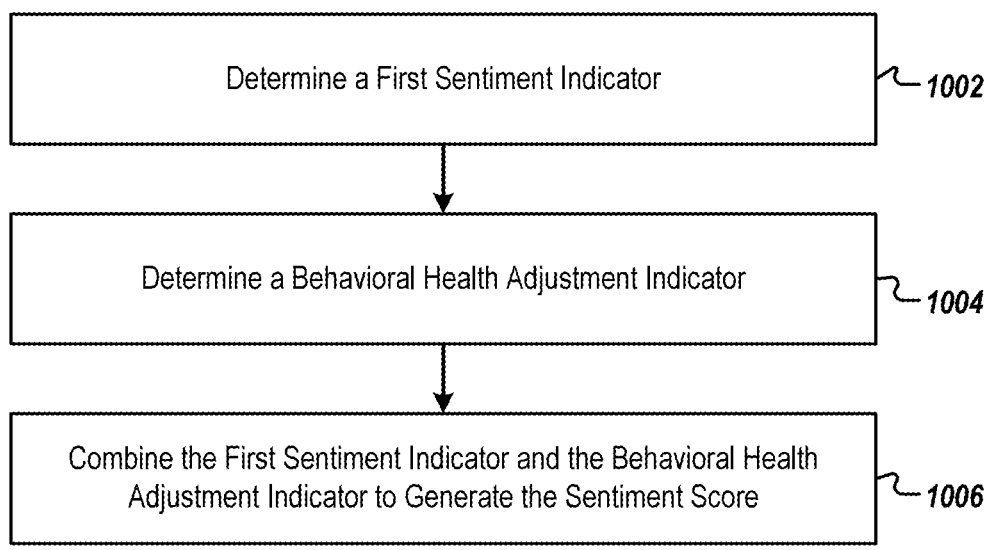
Figure 11:
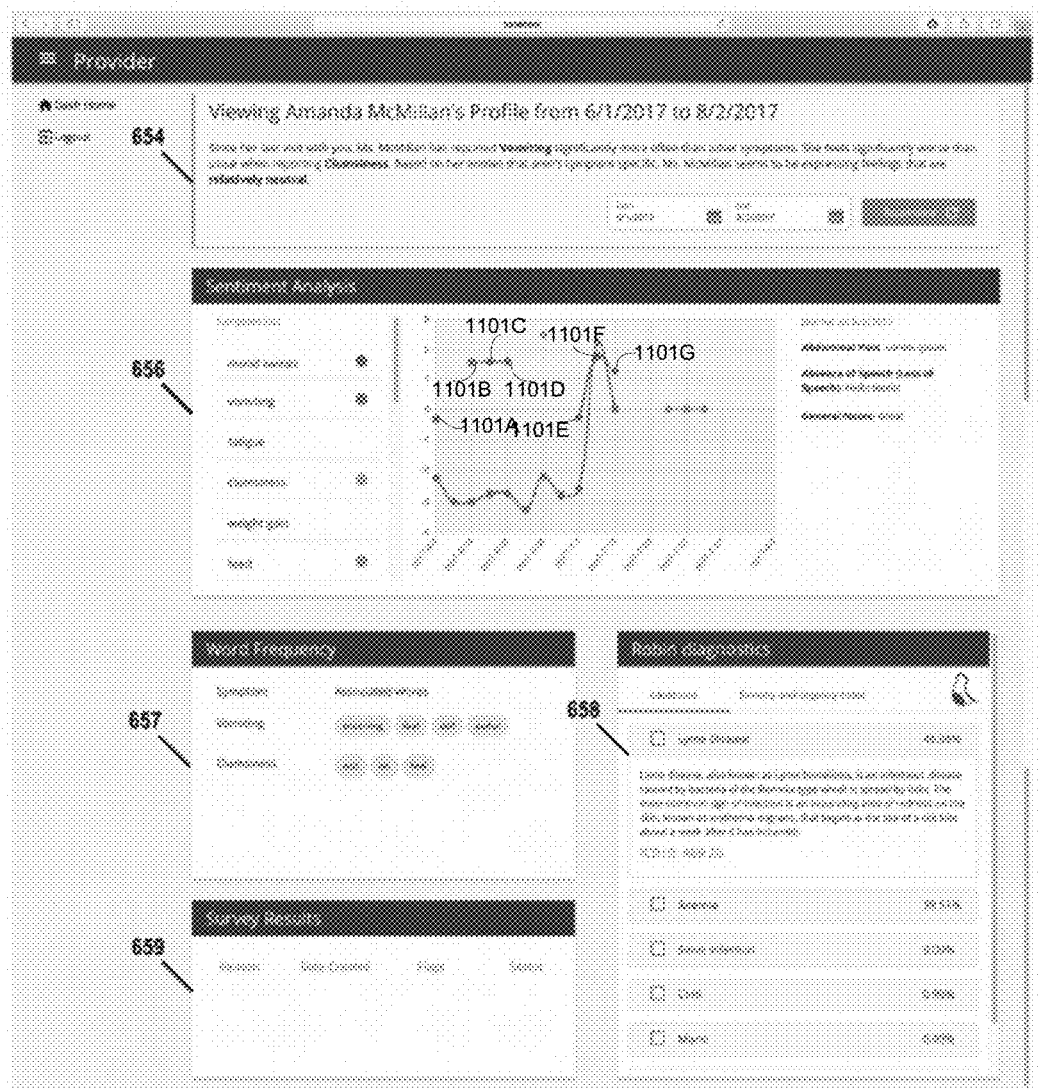
Figure 12:
Figure 13:
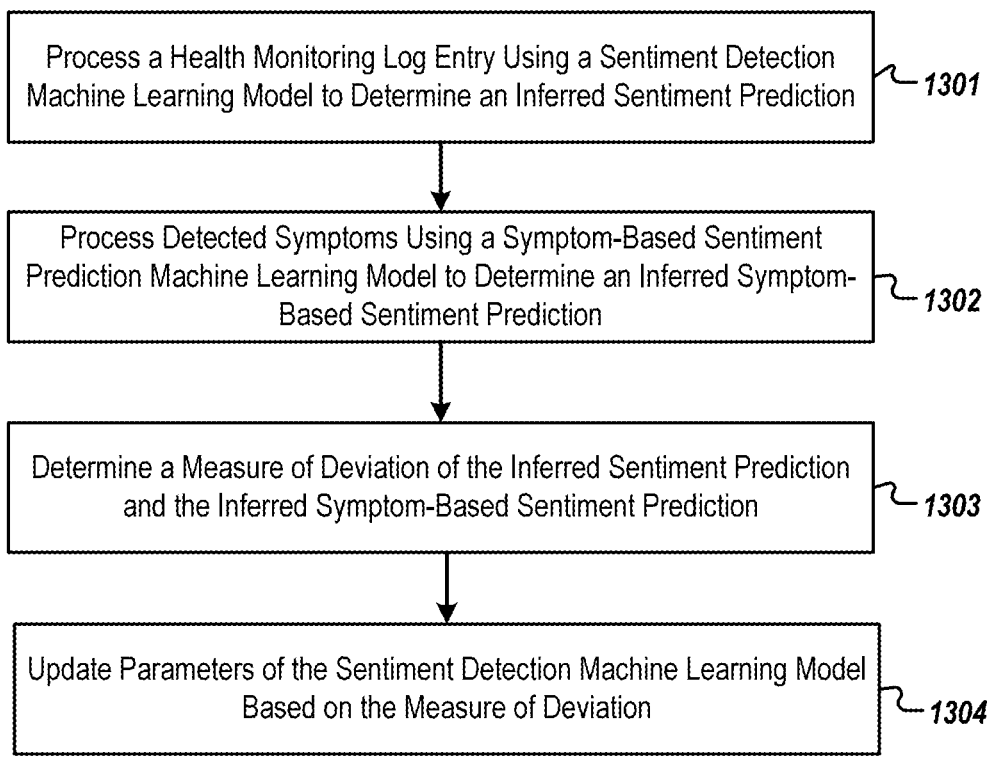

Having thus described certain embodiments of the present invention in general terms, reference will now be made to the accompanying drawings, which are not necessarily drawn to scale, and wherein:

FIG. 1 illustrates a system environment according to one embodiment of the present invention;

FIG. 2 illustrates an example data flow interaction between elements of the system environment of FIG. 1 according to one embodiment;

FIG. 3 illustrates a block diagram of a content analysis server according to one embodiment;

FIG. 4 illustrates a flowchart of example operations executed by a patient input module according to one embodiment;

FIG. 5 illustrates an example user login interface generated by the patient input module according to one embodiment;

FIGS. 6A, 6B, and 7 illustrate example patient input interfaces generated by the patient input module according to one embodiment;

FIG. 8 illustrates a flowchart of example operations executed by a sentiment analysis module according to one embodiment;

FIG. 9 illustrates sentiment analysis, word frequency, and diagnostic condition models generated by the sentiment analysis module according to one embodiment;

FIG. 10 illustrates a flowchart of example operations executed by a provider interface module according to one embodiment;

FIG. 11 illustrates an example patient selector interface generated by the provider interface module according to one embodiment;

FIG. 12 illustrates an example provider analysis interface generated by the provider interface module according to one embodiment; and FIG. 13 is a flowchart diagram of an example process for coordinated training of a sentiment detection machine learning model based on symptom-based data.

DETAILED DESCRIPTION

Some embodiments of the present invention will now be described more fully herein with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

Overview

Various embodiments of the present invention are directed to improved apparatuses, methods, and computer program products for (i) extracting diagnostically relevant data from data records that contain qualitative and/or subjective observations and other relatively unstructured, natural language information and (ii) transforming such data into a human-readable report. In this regard, embodiments of the present invention provide systems, devices, and frameworks that generate an interface in which a user can supply relatively unstructured content that can be captured as a data object, passed to a system capable of performing algorithmic sentiment analysis and other processing to detect and extract diagnostically relevant information, and transformed into a human-readable summary for review and consumption by a diagnostician or other reviewer.

Various implementations described herein arise in the context of a patient-provider relationship, where an individual patient is seeking and obtaining treatment for one or more medical conditions from a medical provider. As such, many of the example implementations described herein use language sets that reflect interactions between patients, doctors, and other healthcare providers. However, it will be appreciated that many of the technical challenges recognized by the inventors and overcome by example implementations of the developments disclosed herein are applicable in other situations and contexts, including but not limited to those involving the diagnosis of conditions in complex electrical, mechanical, computer, and other technological systems.

The inventors of the inventions disclosed herein have recognized that one of the significant technical challenges with the effective and efficient diagnosis, treatment, and remediation of health conditions arises from limitations in the duration and frequency of diagnostic interactions between patients (or other information sources) and healthcare providers (or other reviewers). For example, a given patient may have relatively infrequent, brief visits with his or her doctor, during which the doctor must acquire the diagnostically relevant information from the patient. During those visits, only a limited volume of information can be exchanged. Moreover, the information exchanged often takes the form of a snapshot and/or other expression of the patient's thoughts and expressions at the time of the visit. Furthermore, patients may forget pieces of information that may be diagnostically relevant, and/or fail to recognize that certain information may be diagnostically relevant.

This technical challenge is often compounded by the subjective and personalized nature of a patient's expression of his or her condition. For example, two patients with the same symptoms and same underlying condition may relate the nature, severity, and other information about their symptoms in fundamentally different linguistic terms.

To address these and other technical challenges, the example embodiments described herein are configured to facilitate the aggregation of data describing the patient's conditions, experiences, thoughts, and expressions during the time between visits. In various embodiments, this is accomplished via a system providing a user interface to capture the user interactions over time on a relatively frequent basis. The user-supplied information is then subjected to an algorithmic sentiment analysis via a machine-learning platform. The combination of the algorithmic sentiment analysis and the machine-learning modeling allows for the detection of patient sentiments and/or other diagnostically relevant information on a longitudinal basis that can then be effectively presented to patients and providers.

In certain implementations, a record-keeping platform is provided that allows patients and/or other users to create a record (which may be referred to as a "journal") of their health conditions as they develop on a daily and/or other temporal basis. The journal content is then applied to a sentiment analysis algorithm that analyzes each journal for diagnostically-relevant information. In some embodiments, a model creates a summary of the patient's journals, which outlines in human-readable form the conditions the patient is experiencing and the expressed sentiment with respect to those conditions. As a result, medical staff can efficiently review the aggregated journal entries over a relevant period of time and incorporate the information into diagnostic analyses and/or other decisions regarding a course of treatment. Moreover, in situations where other information (such as patient location, history, biographical information, demographic information and/or the like, for example) is acquired and associated with one or more journal entries, data can be aggregated on a patient-by-patient basis and/or on the basis of potentially relevant shared traits in a manner that allows for the identification of trends amongst relevant groups (e.g., medically-related trends and/or trends in the language and/or sentiments associated with one or more symptoms and/or conditions).

The various embodiments described herein are particularly advantageous in situations involving the analysis and/or review of complex data records featuring natural language portions in network environments (e.g., statements provided by patients regarding their conditions and their feelings regarding those conditions). The review and classification of such records may be aided through the use of a machine learning model that is capable of identifying and associating terms (including but not limited to colloquialisms, subjective impressions, and other non-technical language sets, for example) such that sentiments and/or other diagnostically-relevant information can be detected within such words and phrases. Moreover, certain embodiments may use terms, background facts, and details that are associated with network environments of medical services providers. These embodiments may further reference information, considerations, and other details associated with implementations that may arise in such networks. However, it will be appreciated that embodiments of the invention and example implementations thereof may be applicable and advantageous in a broad range of contexts and situations outside of those related to networks associated with medical services providers.

Various embodiments of the present invention make important contributions to improving efficiency and effectiveness of predictive data analysis in the healthcare space by integrating symptomatic predictive data analysis with sentiment-based predictive data analysis to generate meaningful predictive insights (e.g., meaningful diagnostic predictive insights) about patient conditions. A primary challenge of many existing predictive data analysis solutions in the healthcare space is that symptomatic predictive data analysis fails to capture deviations between patient experience on individual levels as existing models are not powerful enough to capture less dominant real-world patterns on physiological and psychological experiences. Sentiment analysis, which is largely rooted in natural language processing, is theoretically configured to provide independent insights about individual-level conditions and experiences; however, existing sentiment inference models are still not reliable enough as natural language data is not easily conducive to numerical representations needed to perform complex machine learning computations. Furthermore, even when reliably inferred, sentiment insights may simply reflect subjective beliefs about health conditions, rather than objective observations about the noted conditions. Various embodiments of the present invention address the shortcomings of various existing healthcare-related predictive data analysis solutions by integrating predictive insights generated by two typically imperfect sets of models (e.g., symptom-based models and sentiment-based models) to generate more reliable health-related predictive inferences.

Relatedly, in some embodiments, various aspects of the present invention enable symptomatic data to act as ground-truth data that assist sentiment-based inferences and sentiment-based data to act as ground-truth data that assist symptom-based inferences. This dialectic reinforcement mechanism is configured to increase the reliability of predictive inferences performed using the noted integrative approach. This mechanism is further configured to increase computational efficiency and storage-wise efficiency of training machine learning models configured to perform either of symptom-based predictive data analysis and sentiment-based predictive data analysis. This is because, absent utilization of predictive insights determined by using the other predictive method, training of machine learning models configured to perform either of symptom-based predictive data analysis and sentiment-based predictive data analysis would require both greater levels of training data as well as utilization of more computationally complex training techniques and/or utilization of a greater number of training iterations before required training objectives are achieved.

In some embodiments, coordinated integration of symptomatic data and sentiment data in performing predictive data analysis can generate smaller yet more meaningful predictive data analysis conclusions. For example, absent the noted coordinated integration, predictive outputs would document both sentiment fluctuations as well as symptomatic fluctuations, even when such fluctuations are of marginal predictive value. However, by utilizing aspects of the coordinated integration concepts of the present invention, a predictive data analysis system can generate predictive outputs only when sentiment fluctuations correlate with symptomatic fluctuations, an approach that makes the predictive output generated by the predictive data analysis system smaller to store and/or smaller to transmit.

Accordingly, by utilizing aspects of the coordinated integration concepts of the present invention, various embodiments of the present invention increase the storage-wise efficiency and transmission efficiency of various predictive data analysis systems, such as various distributed predictive data analysis systems (e.g., predictive data analysis systems that act as servers in client-server architectures). Because all other things equal smaller amounts of transmitted output data are less likely to cause transmission delays and/or transmission failures than larger amounts of transmitted output data, by reducing the size of predictive outputs generated by distributed predictive data analysis systems according to aspects of the coordinated integration concepts of the present invention, various embodiments of the present invention also increase transmission reliability and network security of various predictive data analysis systems.

EXAMPLE DEFINITIONS

As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention. Further, where a computing device is described herein to receive data from another computing device, it will be appreciated that the data may be received directly from another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to another computing device or may be sent indirectly via one or more intermediary computing devices, such as, for example, one or more servers, relays, routers, network access points, base stations, hosts, and/or the like.

As used herein, the term "circuitry" refers to (a) hardware-only circuit implementations (e.g., implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a microprocessor(s) or a portion of a microprocessor(s), that require software or firmware for operation even if the software or firmware is not physically present. This definition of circuitry applies to all uses of this term herein, including in any claims. As a further example, as used herein, the term circuitry also includes an implementation comprising one or more processors and/or portion(s) thereof and accompanying software and/or firmware. As another example, the term circuitry as used herein also includes, for example, a baseband integrated circuit or applications processor integrated circuit for a mobile phone or a similar integrated circuit in a server, a cellular network device, other network device, and/or other computing device.

As used herein, a "computer-readable storage medium," which refers to a physical storage medium (e.g., volatile or non-volatile memory device), may be differentiated from a "computer-readable transmission medium," which refers to an electromagnetic signal.

As used herein, the terms "user" and/or "client" refer to an individual or entity that is a user of a workstation and/or other device that may be configured to create, access and/or store files within a network environment. For example, a user (which may be, for example, a patient, client, and/or other individual, for example) may be empowered to create, store, and/or otherwise provide content regarding their own condition, the condition of others, and/or the condition of some other system.

The terms "workstation" and/or "user device" refer to computer hardware and/or software that is configured to access and/or otherwise use a service made available by a server. The server is often (but not always) on another computer system, in which case the client device accesses the service by way of a network. Client devices may include, without limitation, smart phones, tablet computers, laptop computers, wearables, personal computers, enterprise computers, and the like.

As used herein, the term "data object" refers to a structured arrangement of data. A "record data object" is a data object that includes one or more sets of data associated with a given data record, such as a user-supplied log entry and/or other data record that is used in connection with one or more sets of user-supplied content. In some example implementations herein, a record data object is a structured arrangement of data that contains a structured data set (such as an identification of a user's selection of one or more list items, for example) and an unstructured data set (such as a set of natural language text, user-supplied video and/or audio, and/or other content, for example).

As used herein, the terms "data set," "information set," and/or other specific "sets" refer to one or more collections of data. One or more information sets may be combined, incorporated into, and/or otherwise structured as a data object.

Example System Environment, Architecture, and Data Flow

FIG. 1 depicts a system environment 100 configured to facilitate the efficient capture, processing, and transformation of diagnostically-relevant data records featuring natural language and/or other relatively unstructured content. As discussed in detail herein, various embodiments of the system environment 100 advantageously provide for the receiving of one or more record data objects associated with a given data record, the extraction of a record image set from the record data object, the rendering in a user interface of a record image from the record image set, the rendering in the user interface of a selectable objects set, the collection of a user action set from the user interface reflecting a plurality of actions performed by a user within the interface, and the applying of the user action set to a training data set associated with a machine learning model, and/or the other actions described, contemplated, and/or otherwise disclosed herein.

As shown in the block diagram of FIG. 1, the system environment 100 is generally comprised of a content analysis system 102, a provider system 104, and a patient system 106. As described in detail herein, the content analysis system 102 is configured to periodically receive and store patient condition data over a period of time (e.g., from the patient system 106), analyze and assess the stored patient condition data, and provide various analyses, models, and assessments of the patient condition data to the patient's health care provider (e.g., via the provider system 104) and to the patient (e.g., via the patient system 106). To this end, various embodiments of the content analysis system 102 are configured to communicate with at least the provider system 104 and one or more remote patient systems 106. It will be appreciated that all of the components shown in FIG. 1 may be configured to communicate over any wired or wireless communication network, including a wired or wireless local area network (LAN), personal area network (PAN), metropolitan area network (MAN), wide area network (WAN), or the like, as well as interface with any attendant hardware, software and/or firmware required to implement said networks (such as network routers and network switches, for example). For example, networks such as a cellular telephone, an 802.11, 802.16, 802.20 and/or WiMAX network, as well as a public network, such as the Internet, a private network, such as an intranet, or combinations thereof, and any networking protocols now available or later developed including, but not limited to, TCP/IP based networking protocols may be used in connection with system environment 100 and embodiments of the invention that may be implemented therein or participate therein.

In the illustrated embodiment of FIG. 1, the content analysis system 102 includes a content analysis server 102A, content analysis database 102B, and a plurality of content analysis system modules 400-700. The content analysis system modules 400-700 may be stored on and executed by the content analysis server 102A. However, in various other embodiments, the content analysis system modules 400-700 may be stored on and executed by any combination of the content analysis server 102A, content analysis database 102B, and/or additional content analysis devices (e.g., PCs, laptops, portable computing devices, cloud-based systems, and the like). Furthermore, the content analysis server 102A may be connected to, for example, any of a number of public and/or private networks, including but not limited to the Internet, the public telephone network, and/or networks associated with particular communication systems or protocols, and may include at least one memory for storing at least application and communication programs.

As discussed in greater detail herein, the content analysis system modules 400-700 are generally configured to receive, process, transform, transmit, and evaluate record data objects, content, and other information associated with such data objects, other data sets, and related interfaces. More specifically, the content analysis system modules 400-700 are configured to capture, store, and analyze data relating to patient conditions and generate analyses and models (as well as graphical user interfaces displaying the same) to provide an enhanced assessment of a patient's health condition.

Referring back to FIG. 1, the content analysis system 102 also includes a content analysis database 102B that may be used to store information associated with record data objects, structured data sets, unstructured data sets, selectable object sets, user action sets, other data sets, interfaces associated with any such data objects or data sets, provider systems, remote user systems, and/or any other information related to use of a user interface to capture user interactions with an interface to provide potentially diagnostically-relevant information. The content analysis database 102B may be accessed by (and configured to receive and store data from) the content analysis system modules 400-700, the content analysis server 102A, and any additional devices implemented as part of the content analysis system. Furthermore, the content analysis database 102B may be used to store any additional information accessed by and/or otherwise associated with the content analysis system 102 and/or its component parts. While FIG. 1 depicts the content analysis database 102B as a single structure, it will be appreciated that the content analysis database 102B may integrated as part of the content analysis server 102A, a related content analysis device, and/or implemented to allow for storage in a distributed fashion and/or at facilities that are physically remote from the each other and/or the other components of the content analysis system 102.

In various other embodiments, the content analysis system 102 may further include additional content analysis devices, which may take the form of a laptop computer, desktop computer, or mobile device, for example, to provide an additional means (other than via a user interface of the content analysis server 102A) to an interface with the other components of the content analysis system 102 and/or other components shown in or otherwise contemplated by the system environment 100. For example, in some example implementations, additional content analysis devices may be used to present a user interface to capture a patient's interactions with the interface in the development of a journal and/or other set of potentially diagnostically-relevant information. Similarly, content analysis devices may be used to facilitate monitoring or interaction with a machine-learning system and/or other system capable of performing an algorithmic sentiment analysis on content received from a user.

As shown in FIG. 1, the system environment 100 further includes a provider system 104 comprising a provider server 104A, provider database 104B, and a provider device 104C. According to various embodiments, the provider server 104A, provider database 104B, and provider device 104C may be operated by a health care provider and are generally configured to communicate with one another and the content analysis system 102 in order to access condition data provided by a patient and assessed by the content analysis system 102. In particular, the provider server 104A may include various system modules configured to facilitate access to information stored with the provider system 104 and content analysis system 102 components. As an example, a health care provider (e.g., a doctor) may use a provider device 102C (e.g., a PC, laptop, or portable computing device) to access the content analysis system 102 via the provider server 104A. In this way, the health care provider can view, read, review, respond to and/or otherwise interact with data and other information stored on the content analysis system 102 (e.g., information and data models concerning a patient's health condition).

The provider database 104B may be accessed by the provider server 104A (and its program modules) and may be used to store any additional information accessed by and/or otherwise associated with the provider system 104 and/or its component parts. While FIG. 1 depicts provider database 104B as a single structure, it will be appreciated that the provider database 104B may additionally or alternatively be implemented to allow for storage in a distributed fashion and/or at facilities that are physically remote from the each other and/or the other components of the provider system 104.

In some example implementations, the provider system 104 may take the form of a web-based interface, a file repository, and/or a related system. Furthermore, while only one provider system 104 is depicted in FIG. 1 in the interest of clarity, it will be appreciated that numerous other such systems may be present in the system environment 100, permitting numerous providers and/or other entities to receive, review, and/or interact with transformed information received from the content analysis system 102.

As shown in FIG. 1, the system environment 100 also includes a remote patient system 106 comprising at least one remote user device 106B. According to various embodiments, the remote user device 106B may comprise, for example, a PC, laptop, or portable computing device. In various embodiments, the content analysis system 102 is configured to interact and communicate with the remote user device 106B to render an interface with which a user/patient may provide structured and/or unstructured data and/or other content relating to their health condition over a period of time. As discussed herein, the content analysis system 102 is configured to compile this received information into one or more relevant record data objects for analysis and transformation. For example, an interface viewable via a remote user device 106B may enable a patient or other user to create, update, and/or otherwise provide a journal, in which the patient is able to describe, using natural language for example, his or her thoughts, feelings, impressions, and/or other expressions of his or her condition. In such an arrangement, a user of a the remote user device 106B need not be co-located with the content analysis system 102 in order to interact with the relevant interface and cause the creation of one or more record data objects While only one remote patient system 106 is depicted in FIG. 1 in the interest of clarity, it will be appreciated that numerous additional such systems may be present in the system environment 100, permitting numerous user/patients to communicate and/or otherwise interact with the content analysis system 102 and/or one or more provider systems 104. As shown in FIG. 1, the remote patient system 106 is capable of communicating with the content analysis system 102 to exchange information associated with interfaces, selectable objects, and record images that the content analysis system 102 may provide when seeking to capture user interactions with respect to a given record data object. For example, the remote patient system 106 may, such as via the capabilities and/or actions of the remote user module 106A and/or remote user device 106B, receive information necessary to render an interactive user interface on a display presented to a user, such that the user may assess files associated with one or more record data objects and related selectable objects.

As depicted in the system environment 100, the content analysis system 102 engages in machine-to-machine communication with the provider system 104 and the remote patient system 106, via one or more networks, to facilitate the processing of record data objects, such that one or more record data objects may be analyzed and transformed in connection with machine learning models based on the interactions of the user within a user interface. FIG. 2 is a block diagram showing an example data flow 300 that may be used in connection with the efficient conversion of user interactions within a user interface (which may be supplying a journal and/or other set of unstructured, natural language and/or set of selectable objects and/or other structured data, for example) into a transformed summary of the user's sentiments and/or other potentially diagnostically-relevant information that can be reviewed efficiently by a service provider and/or other reviewer. As shown in FIG. 2, the content analysis system 102 is configured to receive one or more record data objects from the remote patient system 106 in the form of messages 302A-302N. In some example implementations, the remote patient system 106 may provide a plurality of record data objects to the content analysis system 102, such that the content analysis system 102 may receive record data objects (such as an ongoing journal, for example) on a longitudinal basis via user interfaces associated with one or more user/patients (including but not limited to those who may be operators of one or more remote patient system 106, for example) in a batched manner.

According to various embodiments, upon receipt of a record data object from a remote patient system 106, the content analysis system 102 extracts information from the record data object. The extracted information may take the form of unstructured data, such as natural language information provided by a user, and/or structured data, such as a user's selections of items in a checklist. As a user interacts with the user interface, the content analysis system 102 may collect a set of a user/patient actions that reflects the actions performed by the user within the user interface with respect to one or more prompts and/or checklist items, for example. This user action set may then be applied, along with the data extracted from a record data object, for example, to a model and/or other system incorporated into the content analysis system 102 that is capable of performing a sentiment analysis on the received information and transforming the results of the sentiment analysis and/or other parsing of the received content into a human readable summary of diagnostically-relevant information.

As shown in FIG. 2, depending on the configuration of the content analysis system 102 and the provider system 104, the summary information may be transmitted from the content analysis system 102 to the provider system 104 in the form of message 304 to be applied in connection with providing treatment and/or other services to the user. Based on the content received in message 304, the provider system 104 may be used to communicate directly with the remote patient system 106 via message 306 to accomplish communication between parties.

It will be appreciated that one of the goals of the example embodiments of the invention described and otherwise disclosed herein is to capture diagnostically relevant information on a longitudinal basis and identify trends, on an individualized and/or aggregated basis, that may inform the treatment and/or remediation of one or more conditions experienced by one or more users As such, there may be multiple cycles of instances of messages 302A-302N being transmitted to the content analysis system 102 and multiple instances of message 304 transmitting summary data to provider system 104.

Content Analysis Server and Module Function

The effective and efficient collection, processing, and analysis of diagnostically-relevant data presents a number of technical challenges, particularly in situations involving complex systems. These technical challenges are further compounded in situations where interactions between the relevant system (and individuals involved with such system), diagnosticians, and agents capable of responding to a diagnosed condition, are limited in duration and frequency. Yet, in many modern contexts, temporal, functional, and other limitations have required systems to function at or near peak levels for increased time intervals, with limited opportunities for diagnosis, evaluation, remediation, and repair.

In situations involving the diagnosis and treatment of humans with potential and/or ongoing healthcare needs, these technical challenges are heightened and expanded. In addition to the technical challenges inherent in the diagnosis of any complex system, the effective diagnosis and treatment of people often requires diagnosticians and other service providers to navigate communications barriers, subjective interpretations of events and conditions, and a host of other issues. As an example, healthcare providers generally do not have access to a comprehensive view of a patient's health conditions in between appointments. As a result, details about the patient's condition or symptoms in the period in between visits with a healthcare provider can be overlooked or forgotten by the patient. Indeed, the lack of intimate knowledge of a patient's daily life can often present a fundamental challenge to healthcare providers in making accurate diagnoses.

Accordingly, there is an on-going need in the art for effective and efficient collection, processing, and analysis of diagnostically-relevant data. The inventors of the developments disclosed herein have identified these and other technical challenges, and developed the solutions described and otherwise referenced herein.

FIG. 3 illustrates a block diagram of the content analysis server 102A according to on embodiment. As shown in FIG. 3, the content analysis server 102A includes a processor 202, memory and program storage 204, input/output circuitry 206, communications circuitry 208, and record circuitry 210. The memory and program storage 204 stores various program modules, including a patient input module 400, sentiment analysis module 500, provider interface module 600, and patient interface module 600. According to various embodiments, the content analysis server 102A may be configured to execute any of the operations described herein, including but not limited to those described in connection with FIGS. 4-14.

In various embodiments, the server's processor 202 (and/or co-processors or any other processing circuitry assisting or otherwise associated with the processor) may be in communication with the memory device 204 via a bus for passing information among components of the server. The memory device 204 may be non-transitory and may include, for example, one or more volatile and/or non-volatile memories. In other words, for example, the memory device 204 may be an electronic storage device (e.g., a computer readable storage medium) comprising gates configured to store data (e.g., bits) that may be retrievable by a machine (e.g., a computing device like the processor). The memory device 204 may be configured to store information, data, content, applications, instructions, or the like for enabling the apparatus to carry out various functions in accordance with an example embodiment of the present invention. For example, the memory device 204 could be configured to buffer input data for processing by the processor 202. Additionally or alternatively, the memory device 204 could be configured to store instructions for execution by the processor 202.

In the illustrated embodiments of FIGS. 1-3, the content analysis server 102A is embodied by a computing device. However, in some embodiments, the server 102A may be embodied as a chip or chip set. In other words, the content analysis server 102A may comprise one or more physical packages (e.g., chips) including materials, components, and/or wires on a structural assembly (e.g., a baseboard). The structural assembly may provide physical strength, conservation of size, and/or limitation of electrical interaction for component circuitry included thereon. The content analysis server 102A may therefore, in some cases, be configured to implement an embodiment of the present invention on a single chip or as a single "system on a chip." As such, in some cases, a chip or chipset may constitute means for performing one or more operations for providing the functionalities described herein.

The processor 202 may be embodied in a number of different ways. For example, the processor may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor 202 may include one or more processing cores configured to perform independently. A multi-core processor may enable multiprocessing within a single physical package. Additionally or alternatively, the processor 202 may include one or more processors configured in tandem via the bus to enable independent execution of instructions, pipelining and/or multithreading.

In an example embodiment, the processor 202 may be configured to execute instructions (e.g., program modules) stored in the memory device 204 or otherwise accessible to the processor. Alternatively or additionally, the processor 202 may be configured to execute hard coded functionality. As such, whether configured by hardware or software methods, or by a combination thereof, the processor 202 may represent an entity (e.g., physically embodied in circuitry) capable of performing operations according to an embodiment of the present invention while configured accordingly. Thus, for example, when the processor 202 is embodied as an ASIC, FPGA or the like, the processor 202 may be specifically configured hardware for conducting the operations described herein. Alternatively, as another example, when the processor 202 is embodied as an executor of software instructions, the instructions may specifically configure the processor to perform the algorithms and/or operations described herein when the instructions are executed. However, in some cases, the processor 202 may be a processor of a specific device (e.g., a pass-through display or a mobile terminal) configured to employ an embodiment of the present invention by further configuration of the processor 202 by instructions for performing the algorithms and/or operations described herein. The processor 202 may include, among other things, a clock, an arithmetic logic unit (ALU) and logic gates configured to support operation of the processor.

Referring back to the illustrated embodiment of FIG. 3, the content analysis server optionally includes input/output circuitry 206, which may comprise a user interface that may, in turn, be in communication with the processor 202 to provide output to the user and, in some embodiments, to receive an indication of a user input. As such, the user interface may include a display and, in some embodiments, may also include a keyboard, a mouse, a joystick, a touch screen, touch areas, soft keys, a microphone, a speaker, or other input/output mechanisms. Alternatively or additionally, the processor 202 may comprise user interface circuitry configured to control at least some functions of one or more user interface elements such as a display and, in some embodiments, a speaker, ringer, microphone and/or the like. The processor 202 and/or user interface circuitry comprising the processor may be configured to control one or more functions of one or more user interface elements through computer program instructions (e.g., software and/or firmware) stored on a memory accessible to the processor (e.g., memory device 204, and/or the like).

As shown in FIG. 3, the content analysis server 102A also includes communication circuitry 208. The communication circuitry 208 may be any means such as a device or circuitry embodied in either hardware or a combination of hardware and software that is configured to receive and/or transmit data from/to a network and/or any other device or module in communication with the apparatus. In this regard, the communication interface may include, for example, an antenna (or multiple antennas) and supporting hardware and/or software for enabling communications with a wireless communication network. Additionally or alternatively, the communication interface may include the circuitry for interacting with the antenna(s) to cause transmission of signals via the antenna(s) or to handle receipt of signals received via the antenna(s). In some environments, the communication interface may alternatively or also support wired communication. As such, for example, the communication interface may include a communication modem and/or other hardware/software for supporting communication via cable, digital subscriber line (DSL), universal serial bus (USB) or other mechanisms.

The content analysis server 102A further includes record circuitry 210. The record circuitry 210 includes hardware, firmware, and/or software configured to maintain, manage, and provide access to a record data objects, including but not limited to those received from a remote patient system 106 or provider system 104. The record circuitry 210 may provide an interface, such as an application programming interface (API), which allows other components of a system to extract structured and/or unstructured data sets from record data objects. For example, the record circuitry 210 may extract and/or format a set of selectable objects and/or a set of natural language information from within a record image set, such that the information may be subjected to sentiment analysis and otherwise transformed for review by the provider system 104.

As discussed above, the content analysis server's memory and program storage 204 includes a number of program modules—a patient input module 400, sentiment analysis module 500, provider interface module 600, and patient interface module 600. According to various embodiments, the program modules 400-700 may comprise software, firmware, and/or hardware configured to manage, store, process, and analyze information (such record data objects, natural language information, structured and/or unstructured data sets, and/or indications of user actions, for example) used in connection with providing a user interface to a user that facilitates the performance of one or more actions involved with the identification of diagnostically-relevant information.

According to various embodiments, the patient input module 400 is generally configured to provide an interface through which a patient can input records (e.g., journal entries) of his or her condition periodically over a given time frame. FIG. 4 shows a flow diagram of example operations executed by the patient input module 400 according to one embodiment. As shown in FIG. 4, the example process begins at step 402 where the patient input module 400 generates a user login interface.

FIG. 5 illustrates an example user login interface 450 generated by the patient input module 400. As shown in FIG. 5, the user login interface 450 includes a user name (or email) field 452 and a password field 454. Via the remote user device 106B, a user/patient can enter a user name and password to access the content analysis system 102. Upon receiving a valid username and password combination, the patient input module 400 next moves to step 404 where a patient input interface for the logged-in patient is displayed. According to various embodiments, the patient input interface generated by the patient input module 400 is configured to facilitate repeated, periodic entry of patient condition data over a given time frame.

FIGS. 6A, 6B, and 7 illustrate a patient input interface 460 generated by the patient input module 400 according to various embodiments. As shown in FIG. 6A-7, the patient input interface 460 enables a patient to provide periodic (e.g., daily) "journal entries" of health condition data. In particular, the patient input interface 460 generally provides three options for patient input of log entry data (e.g., three patient input protocols): a symptom selection and description option, a manual log entry option, and a journal chat function. Accordingly, in step 406, the patient input module 400 identifies a user selection of one or more of the three noted patient input protocols.

If the patient input module 400 detects that the user has selected a symptom selection input protocol, the patient input module 400 performs steps 410 and 412. In some embodiments, performing steps 410 and 412 can be described with reference to the patient input interface 460 of FIG. 6A. As shown in FIG. 6A, the patient input interface 460 includes a symptom field 462 to facilitate patient input of symptoms for a given day. In the illustrated embodiment, the patent input module 400 is configured to respond to a user selection of the symptom field 462 by moving to step 410 (shown in FIG. 4). In step 410, the patient input interface 460 provides a symptom drop-down menu 463 (shown in FIG. 6B), from which a user can select a particular symptom he or she is experiencing. The symptom menu 463 may comprises a list of common health-related symptoms, such as: abdominal pain, abnormal facial expressions, absence of speech, acid reflux, acute sinusitis, blurred vision, fatigue, mood swings, vomiting, weight gain, and the like. In response to a user selection of a symptom from the symptom menu 463, the patient input module 400 also presents the user with a symptom description field 466. As shown in FIG. 7, the symptom description field 466 enables the use to enter a natural language description of his or her health condition as it relates to a particular symptom.

The patient input module 400 next moves to step 412, where it records all user-selected symptoms and their associated natural language descriptions in the journal entry for the current day (e.g., as a data record in the content analysis database 102B). This aforementioned steps 410 and 412 are then repeated until the patient has completed recording any particular symptoms for a given journal entry.

If the patient input module 400 detects that the user has selected a manual journal entry input protocol, the patient input module 400 performs steps 420 and 422. In some embodiments, performing steps 420 and 422 can be described with reference to the patient input interface 460 of FIG. 6A. Referring back to FIG. 6A, the patient input interface 460 also includes a general condition description field 467 (e.g., a manual journal entry field). In the illustrated embodiment, the patient input module 400 is configured to respond to a user selection of the condition description field 467 by moving to step 420 (shown in FIG. 4). In step 420, the patient input interface 460—via the condition description field 467—enables the user to enter a natural language description of their present health condition generally (e.g., independent from association with a particular symptom selected from the drop-down menu 463). The patient input module 400 then moves to step 422, where the user's condition description entry is recorded in the journal entry for the current data (e.g., as a data record in the content analysis database 102B). The aforementioned steps are then repeated until the patient has completed recording any general condition descriptions for a given journal entry.

If the patient input module 400 detects that the user has selected a journal chat input protocol, the patient input module 400 performs steps 430 and 432. According to various embodiments, the journal chat function allows a user to conversationally (e.g., through text or voice) log journal entries, take medical surveys, and/or ask medical questions. In step 420, the patient input module 400 launches an interactive journal chat user interface element that is part of a user interface (e.g., a patient input interface, such as the patient input interface 460 of FIGS. 6A-7). The interactive journal chat user interface element enables the user to enter input messages, selections, entries, etc. Upon user entry of user inputs, in step 432, the patient input module 400 records those user inputs and displays any interactive outputs to the user using interactive journal chat user interface element. The aforementioned steps are then repeated until the patient indicates completion of journal entry through the interactive journal chat user interface element.

As will be appreciated from the description herein, the patient input module 400 enables a user to input health condition data—via the patient input interface 430—in order to create daily journal entries reflective of varying symptoms and conditions over a given period of time. As shown in FIGS. 6A-7, the patient input interface 430 displays a journal history 468 showing each of the patient's historical health monitoring logs (e.g., health journal entries). According to various embodiments, the patient's journal entries are stored as data records in the content analysis database 102B. As discussed in greater detail herein, the health condition data stored in the content analysis database 102B can then be accessed by the sentiment analysis module 500, provider interface module 600, and patient interface module 700 to facilitate analysis and modeling of the health condition data.

According to various embodiments, the sentiment analysis module 500 is generally configured to analyze each log entry for a given patient and generate a model outlining the conditions the patient has expressed significant positive and negative sentiment toward. In certain embodiments, the sentiment analysis module 500 may be configured to generate a visual representation of its analysis providing a view of how individual symptoms have progressed over time.

FIG. 8 shows a flow diagram of example operations executed by the sentiment analysis module 500 according to one embodiment.

As shown in FIG. 8, the example process begins at step 802 where the sentiment analysis module 500 obtains log input for a particular patient. For example, the sentiment analysis module 500 may obtain, from the patient input module 400, one or more journal entries from one or more input protocols. In some embodiments, the one or more journal entries include multiple journal entries that all relate to a particular period of time, where the length of the particular period of time may be defined by one or more configuration parameters of the content analysis system 102 (e.g., one or more configuration parameters of the content analysis system 102 stored in the content analysis database 102B of the content analysis system 102).

In some embodiments, the log input for a particular patient includes one or more journal entries and at least one label for at least one log entry from the one or more journal entries. For example, the log input for a particular patient may include a label for a particular log entry that indicates that the log entry relates to a date on which the patient is estimated to have begun taking a particular medication.

In step 804, the sentiment analysis module 500 determines a distribution of top symptoms over a period of time associated with the log input. For example, the sentiment analysis module 500 may determine a top symptom for each period of time (e.g., each day) associated with the log input based on the one or more journal entries in the log input that relate to the particular period of time. In some embodiments, to determine a distribution of top symptoms over a period of time associated with the log input, the sentiment analysis module 500 determines one or more top symptoms for each log entry of one or more journal entries associated with the log input. The sentiment analysis module 500 may determine a top symptom for a log entry by analyzing data (e.g., content data, verbal data, text data, user interaction data such as click speed data or response time data, etc.) associated with the one or more journal entries.

In some embodiments in which the sentiment analysis module 500 determines one or more top symptoms for each log entry of one or more journal entries associated with the log input, the sentiment analysis module 500 may determine a top symptom for a log entry based on data items selected at least in part based on the input protocol associated with the log entry. For example, the sentiment analysis module 500 may determine a top symptom for a particular log entry having a journal chat input protocol based at least in part on an average response time associated with user response while interacting with a journal chat user interface element to input the particular log entry.

In other embodiments in which the sentiment analysis module 500 determines one or more top symptoms for each log entry of one or more journal entries associated with the log input, the sentiment analysis module 500 may determine top symptoms associated with a particular log entry based on a distribution of phrases (e.g., 1-gram phrases or words) in the particular log entry. For example, the sentiment analysis module 500 may determine top symptoms associated with a particular log entry based on at least one of one or more most frequently-used phrases in the log entry and one or more most distinctively used (e.g., most outlier) phrases in the particular log entry relative to the phrases used in one or more other journal entries (e.g., one or more related journal entries, such as one or more journal entries for the particular patient).

In some embodiments, step 804 can be performed with respect to a particular log entry using the various steps of an example process of FIG. 9. The example process of FIG. 9 begins at step 902 when the sentiment analysis module 500 identifies one or more phrases from the phrases in the particular log entry. In some embodiments, the sentiment analysis module 500 identifies all phrases of size n in the particular log entry, where the value of n may be defined by one or more configuration parameters of the content analysis system 102 (e.g., one or more configuration parameters of the content analysis system 102 stored in the content analysis database 102B of the content analysis system 102). For example, the sentiment analysis module 500 identifies all phrases that correspond to entries in a dictionary data structure (e.g., a medical dictionary data structure, such as a symptoms list data structure). As another example, the sentiment analysis module 500 identifies all phrases of size n that that correspond to entries in a dictionary data structure (e.g., a medical dictionary data structure, such as a symptoms list data structure), where the value of n may be defined by one or more configuration parameters of the content analysis system 102.

In step 904, the sentiment analysis module 500 determines m most frequently-used identified phrases in the particular log entry, where the value of m may be defined by one or more configuration parameters of the content analysis system 102 (e.g., one or more configuration parameters of the content analysis system 102 stored in the content analysis database 102B of the content analysis system 102). In some embodiments, the sentiment analysis module 500 may generate an array of m most frequently-used identified phrases in the particular log entry whose zeroth element is an array of the most frequently-used identified phrases in text, and whose first element represents the statistical significance of those frequently-used identified phrases. For example, the first element of the array may have a value of 2 if all the frequently-used identified phrases in the zeroth element are 2 standard deviations above a norm of frequency for the particular log entry, a value of 1 if all of the frequently-used identified phrases in the zeroth element are 1.5 standard deviations above, and a value of 0 if all of the frequently-used identified phrases in the zeroth element are among the top five most frequent words. The sentiment analysis module 500 may generate the described array by, for example, processing the particular log entry, e.g., processing the particular log entry using one or more text processing and/or natural language processing techniques.

In step 906, the sentiment analysis module 500 determines j most distinctively-used (e.g., most outlier) identified phrases in the log entry relative to the phrases used in one or more other journal entries (e.g., one or more related journal entries, such as one or more journal entries for the particular patient), where the value of j may be defined by one or more configuration parameters of the content analysis system 102 (e.g., one or more configuration parameters of the content analysis system 102 stored in the content analysis database 102B of the content analysis system 102). In some embodiments, the sentiment analysis module 500 generates an array whose zeroth element is an array of frequently-used phrases form the log entry and whose first element represents a method by which those phrases are calculated. For example, the first element of the array may have a value of 2 if all the frequently-used identified phrases in the zeroth element are 2 standard deviations above a norm of frequency for the particular log entry, a value of 1 if all of the frequently-used identified phrases in the zeroth element are 1.5 standard deviations above, and a value of 0 if all of the frequently-used identified phrases in the zeroth element are among the top five most frequent words. The sentiment analysis module 500 may generate the described array by, for example, processing the particular log entry using one or more text processing and/or natural language processing techniques.

In step 908, the sentiment analysis module 500 generates top systems for the particular log entry based on at least one of the determined frequently-used phrases determined in step 904 and the distinctively-used phrases determined in step 906. In some embodiments, the sentiment analysis module 500 determines one or more symptoms for each combination of one or more phrases, where each phrase of the one or more phrases may be a frequently-used phrase determined in step 904, a distinctively-used phrase determined in step 906, or both. For example, the sentiment analysis module 500 may determine that the phrase "throw up" corresponds to a nausea symptom. As another example, the sentiment analysis module 500 may determine that the combination of the phrase "I was happy" and "I was upset" corresponds to the mood-swing symptom. In some of the embodiments in which the sentiment analysis module 500 determines one or more symptoms for each combination of one or more phrases, the sentiment analysis module 500 may map phrases to symptoms based on a dictionary data structure (e.g., a medical dictionary data structure, such as a symptoms list data structure).

Returning to FIG. 8, in step 806, the sentiment analysis module 500 determines a distribution of a sentiment scores over a period of time associated with the log input. For example, the sentiment analysis module 500 may determine a sentiment score for each period of time (e.g., each day) associated with the log input based on the one or more journal entries in the log input that relate to the particular period of time. In some embodiments, to determine a distribution of top symptoms over a period of time associated with the log input, the sentiment analysis module 500 determines one or more sentiment indicators for each log entry of one or more journal entries associated with the log input.

In some embodiments, step 806 can be performed with respect to a particular log entry using the various steps of an example process of FIG. 10. The example process of FIG. 10 begins at step 1002 by determining a first sentiment indicator for the particular log entry. For example, the sentiment analysis module 500 may process the particular log entry in accordance with a sentiment analysis module (e.g., a sentiment analysis module that uses natural language processing, such as the salient natural language processing module) to generate a first sentiment indicator for the particular log entry. The first sentiment indicator for the particular log entry may include an estimation of negativity of mood of the user while inputting the particular log entry.

In some embodiments, the sentiment analysis module 500 may determine the first sentiment indicator for the particular log entry based on at least a portion of the content of the particular log entry and/or one or more data items associated with the particular log entry (e.g., content data, verbal data, text data, user interaction data such as click speed data or response time data, etc.). In other embodiments, the sentiment analysis module 500 may determine the first sentiment indicator for the particular log entry based on an aggregation (e.g., a summation and/or an averaging) of one or more sentiment indicators each of which indicate an aspect of negativity, upset mood, and/or unhealthy condition estimation of the user while inputting the particular log entry.

In step 1004, the sentiment analysis module 500 determines a behavioral health adjustment factor for the particular log entry. The behavioral health indicator for the particular log entry may include an estimation of a behavioral health metric of the patient while inputting particular log entry. For example, the sentiment analysis module 500 may process the particular log entry in accordance with a behavioral health analysis module (e.g., a behavioral health analysis module that uses natural language processing, such as the salient natural language processing module) to generate a behavioral health adjustment factor for the particular log entry. In some embodiments, the sentiment analysis module 500 may determine the behavioral health adjustment factor for the particular log entry based on at least a portion of the content of the particular log entry and/or one or more data items associated with the particular log entry (e.g., content data, verbal data, text data, user interaction data such as click speed data or response time data, etc.). In other embodiments, the sentiment analysis module 500 may determine the behavioral health adjustment factor for the particular log entry based on an aggregation (e.g., a summation and/or an averaging) of one or more sentiment indicators each of which indicate an aspect of the behavioral health of the user while inputting the particular log entry.

In step 1006, the sentiment analysis module 500 proceeds to combine the first sentiment indicator for the particular log entry determined in step 1002 and the behavioral health adjustment indicator for the particular log entry determined in step 1004 to generate the sentiment score for the particular log entry. In some embodiments, the sentiment analysis module 500 adjusts the first sentiment indicator for the particular log entry based on the behavioral health adjustment indicator for the particular log entry to generate the sentiment score for the particular log entry. For example, the noted adjustment may be performed based on a particular adjustment relationship that incorporates a correlation relationship between each of the first sentiment indicator and the behavioral health adjustment indicator and the overall health-related sentiment of a patient.

In some embodiments, combining the first sentiment indicator for the particular log entry and the behavioral health adjustment indicator for the particular log entry to generate the sentiment score for the particular log entry enables the sentiment analysis module 500 to generate a comprehensive sentiment score for the particular log entry that takes into account both of an expressive sentiment indicator (e.g., the first sentiment indicator for the particular log entry determined in step 1002) and an internal sentiment indicator (e.g., the behavioral health adjustment indicator for the particular log entry determined in step 1004).

Returning to FIG. 8, in step 808, the sentiment analysis module 500 generates an aggregate health distribution for the log input by combining the distribution of top symptoms for the particular log input determined in step 804 and the distribution of sentiment scores for the log input determined in step 806. In some embodiments, the sentiment analysis module 500 generates as an output a temporal health distribution data structure that indicates, for each time unit in a particular period of time including multiple time units (e.g., a period of two weeks including 14 days), the top symptoms for the time unit and the sentiment score for the time unit. In other embodiments, in addition to or instead of the temporal health distribution data structure, the sentiment analysis module 500 further generates one or more other outputs that each indicate one or more of most frequently-used phrases in the log input, top symptoms extracted from the log input, one or more medical diagnoses determined from the log input, and/or one or more medical recommendations (e.g., one or more prescriptions) determined based on the log input.

Once generated, the provider interface module 600 and the patient interface module 700 may utilize at least some outputs of the sentiment analysis module 500 to generate patient health interfaces for medical providers and patients respectively. Examples such patient health interfaces are provided in the patient health interface 650 of FIG. 11 (which may be generated for a medical provider by the provider interface module 600) and the patient health interface 470 of FIG. 12 (which may be generated for a patient by the patient interface module 700).

As depicted in FIG. 11, the patient health interface 650 includes a user interface element 654 that indicates a verbal description of a distribution of top symptoms of a patient within a particular period of time identified based on user input. The contents of the user interface element 654 may be generated based on the distribution of top symptoms during the particular period of time identified based on user input, e.g., using the operations discussed in reference to step 804 of FIG. 8.

The user interface 650 further includes a user interface element 656. The user interface element 656 includes a symptom list sub-element, a graph sub-element, and a journal description sub-element. The symptom list sub-element of the user interface element 656 is configured to act as a guide to the graph sub-element of the user interface element 656. For example, the symptom list sub-element indicates, for each symptom of at least some of the symptoms whose occurrence is depicted by the graph sub-element, a corresponding color for points associated with the respective symptom in the graph sub-element. The user interface element 656 may be a component of a portion of the components of an aggregate distribution user interface as discussed herein.

The graph sub-element of the user interface element 656 includes a range of time units on the x axis and a range of sentiment scores on the y axis. Each individual graph depicted by the graph sub-element indicates a consecutive occurrence of a particular top symptom across one or more time units as well as one or more sentiment scores associated with the noted consecutive occurrence. For example, the example graph sub-element in FIG. 11 depicts that the symptom mood swings (denoted by the points 1101A-G marked by a first color, as noted in the symptom list sub-element) has occurred in three time units between 2017/08/14 and 2017/8/21, each time with a sentiment score of 1.5

The journal description sub-element of the user interface element 656 indicates, for each symptom of at least some of the symptoms whose occurrence is depicted by the graph sub-element, an indication of particular phrases in a particular log entry that conform to the particular symptom. For example, the example journal description sub-element of FIG. 11 indicates that, in the particular log entry associated with the date of Aug. 2, 2017, the phrase "Lorem Ipsum" corresponds to an occurrence of the abdominal pain symptom in the patient associated with the particular log entry.

The user interface 650 further includes a user interface element 657 that indicates identified symptoms associated with a particular period of time identified based on user input and the associated words for each symptom in the journal entries for the particular period of time. The contents of the user interface elements may be generated based on the associations between at least some of the frequently-used phrases determined in step 904 of FIG. 9 and/or at least some of the distinctively-used phrases determined in step 906 of FIG. 9 with at least some of the top systems generated in step 908 of FIG. 9

The user interface 650 further includes a user interface element 658 that provides information about possible medical diagnoses based on the journal entries for the particular period of time identified based on user input. To generate the user interface element 658, the provider interface module 600 may first determine, based on the aggregate health distribution generated in step 808 of FIG. 8, one or more predicted diseases for the patient. For example, the provider interface module 600 may make this determination using a medical diagnosis software that generates, based on occurrence of one or more symptoms in health conditions of a patient, one or more predicted diseases for the patient. After determining one or more predicted diseases for the patient, the provider interface module 600 may obtain (e.g., from a third party software and/or third database and using one or more application programming interface (API) calls to the third software and/or third party database) health information associated with the one or more predicted diseases for the patient (e.g., symptoms of the diseases, the remedies for the diseases, the risk factors associated with the diseases, etc.). The provider interface module 600 may use the obtained information to generate the user interface element 658.

The user interface 650 further includes a user interface element 659 that provides results of any medical surveys conducted by a particular patient (e.g., the medical surveys completed by the particular patient during the particular period of time). The content of the user interface element 659 may be generated by processing results of one or more past medical surveys by the particular patient. In some embodiments, the past medical surveys may have been generated based on past patient input, such as past patient input in the form of health monitoring logs. For example, the past medical surveys may have been communicated to the patient using a journal chat function.

Moreover, as depicted in FIG. 12, the patient health interface 470 includes a user interface element 472 that includes sentiment analysis information, a user interface element 475 that includes information related to medical care facilities available to the patient given the identified conditions of the patient, and a user interface element 477 that provides a map of a geographical location of the medical care facilities indicated in the user interface element 475 of the patient health interface 470. In some embodiments, to generate the user interface element 477, the patient interface module 700 may access (e.g., using one or more API calls) at least one database of medical practitioners that provides, for each medical condition, one or more medical practitioners deemed skilled to address the medical condition as well as one database of various geographic locations, such as a database of geographic locations associated with a navigational software that uses global positioning system (GPS).

The sentiment analysis module 500 may also provide outputs to a journal chat function user interface element that the journal user interface element presents as outputs to a user. For example, the sentiment analysis module 500 may (based on one or more rules and/or based on a machine learning logic) generate an interactive response to a user input entered using the journal chat function user interface element based on at least one of a distribution of top symptoms determined using the user input and/or a distribution of sentiment scores determined using the user input. In some embodiments, the journal chat function user interface element may display the generated outputs as interactive messages to a user in response to the received user input.

In some embodiments, at least some of the operations of the sentiment analysis module 500 may be performed a sentiment detection machine learning model. For example, at least one of the behavioral sentiment operations of the sentiment analysis module 500 may be performed by a sentiment detection machine learning model. As another example, at least one of the phrase-based sentiment detection operations of the sentiment analysis may be performed by a sentiment detection machine learning model. FIG. 13 is a flowchart diagram of an example process 1300 for coordinated training of a sentiment detection machine learning model based on symptom-based data.

The process 1300 begins at step/operation 1301 when a training engine of the sentiment analysis module 500 processes a health monitoring log entry for a particular time unit using the sentiment detection machine learning model in order to determine an inferred sentiment prediction for the particular time unit. In some embodiments, the training engine processes the entire natural language text of the health monitoring log entry using the sentiment detection machine learning model in order to determine the inferred sentiment prediction for the particular time unit. In some embodiments, the training engine processes one or more distinctively-used phrases of the health monitoring log entry using the sentiment detection machine learning model in order to determine the inferred sentiment prediction for the particular time unit. In some embodiments, the training engine processes one or more frequently-used phrases of the health monitoring log entry using the sentiment detection machine learning model in order to determine the inferred sentiment prediction for the particular time unit.

The sentiment detection machine learning model may be a machine learning model configured to generate discrete or continuous sentiment scores for a time unit based on natural language input data associated with the time unit. In some embodiments, the sentiment detection machine learning model may utilize a pretrained machine learning model (e.g., a Bidirectional Encoder Representations from Transformers (BERT) model) to generate numeric encodings for the natural language input associated with the time unit. In embodiments where the sentiment detection machine learning model may utilize a pretrained machine learning model to generate numeric coding for the natural language input associated with the time unit, the pretrained machine learning model may have been generated by applying transfer learning to a generic pretrained machine learning model, such as to a BERT model.

At step/operation 1302, the training engine processes detected symptoms for the particular time unit (e.g., sentiment data determined at step 804) using a symptom-based sentiment detection machine learning model in order to determine an inferred symptom-based sentiment prediction for the particular time unit. The symptom-based sentiment detection machine learning model may be a model that is configured to generate expected sentiment scores for a physiological condition based on symptomatic feature data associated with the physiological condition.

In some embodiments, the symptom-based sentiment detection machine learning model may include a multi-dimensional symptom-based condition mapping space that maps a group of observed conditions based on a degree of presence of particular symptoms during observation of those observed conditions. For example, the multi-dimensional symptom-based condition mapping space may map a particular observed condition that is associated with a ground-truth sentiment score based on a degree of presence of nausea, dizziness, fever, and thirst in those noted conditions. The training engine may be configured to utilize the multi-dimensional symptom-based condition mapping space in order to determine the inferred symptom-based sentiment prediction for the particular time unit. To do so, the training engine may map the particular time unit to the multi-dimensional symptom-based condition mapping space based on presence of the identified symptoms of the particular time unit. Afterward, the training engine may aggregate the ground-truth sentiment scores for observed conditions whose mappings in the multi-dimensional symptom-based condition mapping space is deemed sufficiently proximate to the mapping of the particular time unit in order to determine the inferred symptom-based sentiment prediction for the particular time unit.

At step/operation 1303, the training engine determines a measure of deviation of the inferred sentiment prediction for the particular time unit and the inferred symptom-based sentiment prediction for the particular time unit. In other words, the training engine may utilize the inferred symptom-based sentiment prediction for the particular time unit as a ground-truth value to evaluate the accuracy/reliability of the inferred sentiment prediction for the particular time unit. The measure of deviation may be an error function (e.g., a cross-entropy error function) determined across a group of time units.

At step/operation 1304, the training engine updates parameters of the sentiment detection machine learning model based on the measure of deviation. In some embodiments, the training engine adopts a combination of parameters that minimizes an error function determined based on the measure of deviation as the trained parameters of the sentiment detection machine learning model. In some embodiments, the training engine adopts a combination of parameters that maximizes a utility function determined based on the measure of deviation as the trained parameters of the sentiment detection machine learning model. In some embodiments, to optimize an error/reward function determined based on the measure of deviation, the training engine utilizes an optimization algorithm, such as gradient descent, gradient descent with backpropagation, or gradient descent with backpropagation through time.

Additional Implementation Details

Although an example processing system has been described in FIG. 2, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs (e.g., one or more modules of computer program instructions) encoded on computer storage medium for execution by, or to control the operation of, information/data processing apparatus. Alternatively, or in addition, the program instructions can be encoded on an artificially-generated propagated signal (e.g., a machine-generated electrical, optical, or electromagnetic signal) which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory or a random access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data (e.g., magnetic, magneto-optical disks, or optical disks). However, a computer need not have such devices. Devices suitable for storing computer program instructions and information/data include all forms of non-volatile memory, media and memory devices, including by way of example semiconductor memory devices (e.g., EPROM, EEPROM, and flash memory devices); magnetic disks (e.g., internal hard disks or removable disks); magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a LAN and WAN, an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described herein in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for generating one or more health-related predictive inferences from one or more health monitoring logs, the computer-implemented method comprising:

determining, by one or more processors and based at least in part on the one or more health monitoring logs, a first distribution of symptomatic prediction labels over a first period of time associated with the one or more health monitoring logs, wherein the first distribution of symptomatic prediction labels comprises top symptoms for each of the one or more health monitoring logs;

generating, by the one or more processors and using a sentiment detection machine learning model and the one or more health monitoring logs, a second distribution of extracted sentiment scores over the first period of time, wherein the second distribution of extracted sentiment scores comprises an extracted sentiment score for each of the one or more health monitoring logs;

generating, by the one or more processors and based at least in part on the first distribution and the second distribution, an aggregate distribution of inferred health-related predictions over the first period of time, wherein the aggregate distribution of inferred health-related predictions comprises a top symptom and extracted sentiment score for each of the one or more health monitoring logs; and providing, by the one or more processors, a presentation for display via a user interface, wherein the presentation comprises the aggregate distribution.

2. The computer-implemented method of claim 1, wherein determining the first distribution comprises:

determining, for each health monitoring log of the one or more health monitoring logs, one or more extracted symptoms;

identifying, for each time unit of one or more time units associated with the first period of time, one or more first health monitoring logs of the one or more health monitoring logs associated with the time unit;

determining, for each time unit of the one or more time units, one or more first extracted symptoms, wherein the one or more first extracted symptoms for a time unit of the one or more time units include each of the one or more extracted symptoms for a first health monitoring log of the one or more first health monitoring logs that is associated with the time unit; and combining each one or more first extracted symptoms associated with a time unit of the one or more time units to determine the first distribution.

3. The computer-implemented method of claim 2, wherein determining the one or more extracted symptoms for a first health monitoring log of the one or more journal entries comprises:

identifying one or more relevant phrases in the first health monitoring log;

determining one or more selected phrases for the first health monitoring log comprising at least one of a first number of relevant phrases from the one or more relevant phrases that are most frequently used in the first health monitoring log and a second number of relevant phrases from the one or more relevant phrases that are most distinctively used in the first health monitoring log relative to other journal entries in the one or more other journal entries; and determining the one or more extracted symptoms based at least in part on the one or more selected phrases.

4. The computer-implemented method of claim 3, wherein determining the one or more extracted symptoms based at least in part on the one or more selected phrases comprises:

for each selected phrase of the one or more selected phrases, determining a corresponding extracted symptom of the one or more extracted symptoms.

5. The computer-implemented method of claim 1, wherein determining the second distribution of extracted sentiment scores over the first period of time comprises:

determining, for each health monitoring log of the one or more health monitoring logs, one or more sentiment indicators;

identifying, for each time unit of one or more time units associated with the first period of time, one or more first health monitoring logs of the one or more health monitoring logs associated with the time unit;

determining, for each time unit of the one or more time units, one or more first sentiment scores, wherein the one or more first sentiment scores for a time unit of the one or more time units includes each of the one or more sentiment indicators associated with a first health journal of the one or more first health journals that is associated with the time unit; and combining each one or more first sentiment scores associated with a time unit of the one or more time units to determine the second distribution.

6. The computer-implemented method of claim 5, wherein the one or more sentiment indicators for a first health monitoring log of the one or more health monitoring logs include one or more general sentiment indicators for the first health monitoring log and one or more behavioral health sentiment indicators for the first health monitoring log.

7. The computer-implemented method of claim 5, wherein the one or more sentiment indicators for a first health monitoring log of the one or more health monitoring logs include one or more expressive sentiment indicators for the first health monitoring log and one or more internal health sentiment indicators for the first health monitoring log.

8. The computer-implemented method of claim 1, wherein generating the aggregate distribution of inferred health-related predictions over the first period of time comprises generating a graph object that depicts, for each consecutive occurrence of a first symptom associated with the one or more health monitoring logs over one or more time units in the first period of time, a corresponding semantic score from the second distribution.

9. The computer-implemented method of claim 1, wherein generating the second distribution comprises:

determining, for each occurrence of an extracted symptom on a first time unit of the one or more time units, a sentiment score based at least in part on one or more sentiment indicators.

10. The computer-implemented method of claim 1, wherein generating the second distribution comprises:

determining, for all occurrences of an extracted symptom on a first time unit of the one or more time units, a sentiment score based at least in part on one or more sentiment indicators.

11. The computer-implemented method of claim 1, further comprising generating one or more medical diagnoses based at least in part on the aggregate distribution.

12. The computer-implemented method of claim 1, further comprising generating one or more medical recommendations based at least in part on the aggregate distribution.

13. An apparatus comprising at least one processor and at least one memory including program code, the at least one memory and the program code configured to, with the processor, cause the apparatus to at least:

determine, based at least in part on the one or more health monitoring logs, a first distribution of symptomatic prediction labels over a first period of time associated with the one or more health monitoring logs, wherein the first distribution of symptomatic prediction labels comprises top symptoms for each of the one or more health monitoring logs;

generate, using a sentiment detection machine learning model and the one or more health monitoring logs, a second distribution of extracted sentiment scores over the first period of time, wherein the second distribution of extracted sentiment scores comprises an extracted sentiment score for each of the one or more health monitoring logs;

generate, based at least in part on the first distribution and the second distribution, an aggregate distribution of inferred health-related predictions over the first period of time, wherein the aggregate distribution of inferred health-related predictions comprises a top symptom and extracted sentiment score for each of the one or more health monitoring logs; and provide a presentation for display via a user interface, wherein the presentation comprises the aggregate distribution.

14. The apparatus of claim 13, wherein determining the first distribution comprises:
   determining, for each health monitoring log of the one or more health monitoring logs, one or more extracted symptoms;
   identifying, for each time unit of one or more time units associated with the first period of time, one or more first health monitoring logs of the one or more health monitoring logs associated with the time unit;
   determining, for each time unit of the one or more time units, one or more first extracted symptoms, wherein the one or more first extracted symptoms for a time unit of the one or more time units include each of the one or more extracted symptoms for a first health monitoring log of the one or more first health monitoring logs that is associated with the time unit; and
   combining each one or more first extracted symptoms associated with a time unit of the one or more time units to determine the first distribution.

15. The apparatus of claim 14, wherein determining the one or more extracted symptoms for a first health monitoring log of the one or more journal entries comprises:
   identifying one or more relevant phrases in the first health monitoring log;
   determining one or more selected phrases for the first health monitoring log comprising at least one of a first number of relevant phrases from the one or more relevant phrases that are most frequently used in the first health monitoring log and a second number of relevant phrases from the one or more relevant phrases that are most distinctively used in the first health monitoring log relative to other journal entries in the one or more other journal entries; and
   determining the one or more extracted symptoms based at least in part on the one or more selected phrases.

16. The apparatus of claim 15, wherein determining the one or more extracted symptoms based at least in part on the one or more selected phrases comprises:
   for each selected phrase of the one or more selected phrases, determining a corresponding extracted symptom of the one or more extracted symptoms.

17. A computer program product comprising at least one non-transitory computer-readable storage medium having computer-readable program code portions stored therein, the computer-readable program code portions configured to:
   determine, based at least in part on the one or more health monitoring logs, a first distribution of symptomatic prediction labels over a first period of time associated with the one or more health monitoring logs, wherein the first distribution of symptomatic prediction labels comprises top symptoms for each of the one or more health monitoring logs;
   generate, using a sentiment detection machine learning model and the one or more health monitoring logs, a second distribution of extracted sentiment scores over the first period of time, wherein the second distribution of extracted sentiment scores comprises an extracted sentiment score for each of the one or more health monitoring logs;
   generate, based at least in part on the first distribution and the second distribution, an aggregate distribution of inferred health-related predictions over the first period of time, wherein the aggregate distribution of inferred health-related predictions comprises a top symptom and extracted sentiment score for each of the one or more health monitoring logs; and
   provide a presentation for display via a user interface, wherein the presentation comprises the aggregate distribution.

18. The computer program product of claim 17, wherein determining the first distribution comprises:
   determining, for each health monitoring log of the one or more health monitoring logs, one or more extracted symptoms;
   identifying, for each time unit of one or more time units associated with the first period of time, one or more first health monitoring logs of the one or more health monitoring logs associated with the time unit;
   determining, for each time unit of the one or more time units, one or more first extracted symptoms, wherein the one or more first extracted symptoms for a time unit of the one or more time units include each of the one or more extracted symptoms for a first health monitoring log of the one or more first health monitoring logs that is associated with the time unit; and
   combining each one or more first extracted symptoms associated with a time unit of the one or more time units to determine the first distribution.

19. The computer program product of claim 18, wherein determining the one or more extracted symptoms for a first health monitoring log of the one or more journal entries comprises:
   identifying one or more relevant phrases in the first health monitoring log;
   determining one or more selected phrases for the first health monitoring log comprising at least one of a first number of relevant phrases from the one or more relevant phrases that are most frequently used in the first health monitoring log and a second number of relevant phrases from the one or more relevant phrases that are most distinctively used in the first health monitoring log relative to other journal entries in the one or more other journal entries; and
   determining the one or more extracted symptoms based at least in part on the one or more selected phrases.

20. The computer program product of claim 19, wherein determining the one or more extracted symptoms based at least in part on the one or more selected phrases comprises:
   for each selected phrase of the one or more selected phrases, determining a corresponding extracted symptom of the one or more extracted symptoms.

* * * * *